United States Patent [19]

Stavinoha, Jr. et al.

[11] Patent Number: 5,117,012

[45] Date of Patent: May 26, 1992

[54] RECOVERY OF 3,4-EPOXY-1-BUTENE FROM 1,3-BUTADIENE OXIDATION EFFLUENTS

[75] Inventors: Jerome L. Stavinoha, Jr.; John D. Tolleson, both of Longview, Tex.

[73] Assignee: Eastman Kodak Company, Rochester, N.Y.

[21] Appl. No.: 772,750

[22] Filed: Oct. 7, 1991

[51] Int. Cl.$^5$ ................ C07D 301/10; C07D 301/32
[52] U.S. Cl. ..................... 549/538; 549/534; 549/541
[58] Field of Search ................... 549/538, 534

[56] References Cited

U.S. PATENT DOCUMENTS

| | | | |
|---|---|---|---|
| 2,653,952 | 9/1953 | Egbert | 549/538 |
| 3,312,719 | 4/1967 | Hullstrung et al. | 549/534 |
| 4,879,396 | 11/1989 | Ozero | 549/534 |
| 4,897,498 | 1/1990 | Monnier et al. | 549/534 |
| 4,950,773 | 8/1990 | Monnier et al. | 549/534 |

Primary Examiner—J. E. Evans
Attorney, Agent, or Firm—J. Frederick Thomsen; William P. Heath, Jr.

[57] ABSTRACT

Disclosed are processes for the manunfacture of 3,4-epoxy-1-butene (EpB) and, particularly, for the recovery of EpB from an epoxidation effluent comprising EpB, butadiene, oxygen and an inert gas obtained by the selective epoxidation of butadiene with an oxygen-containing gas in the presence of a catalyst and an inert gas. EpB is separated from the effluent by means of an absorption process using liquid butadiene as the absorbent material.

12 Claims, 1 Drawing Sheet

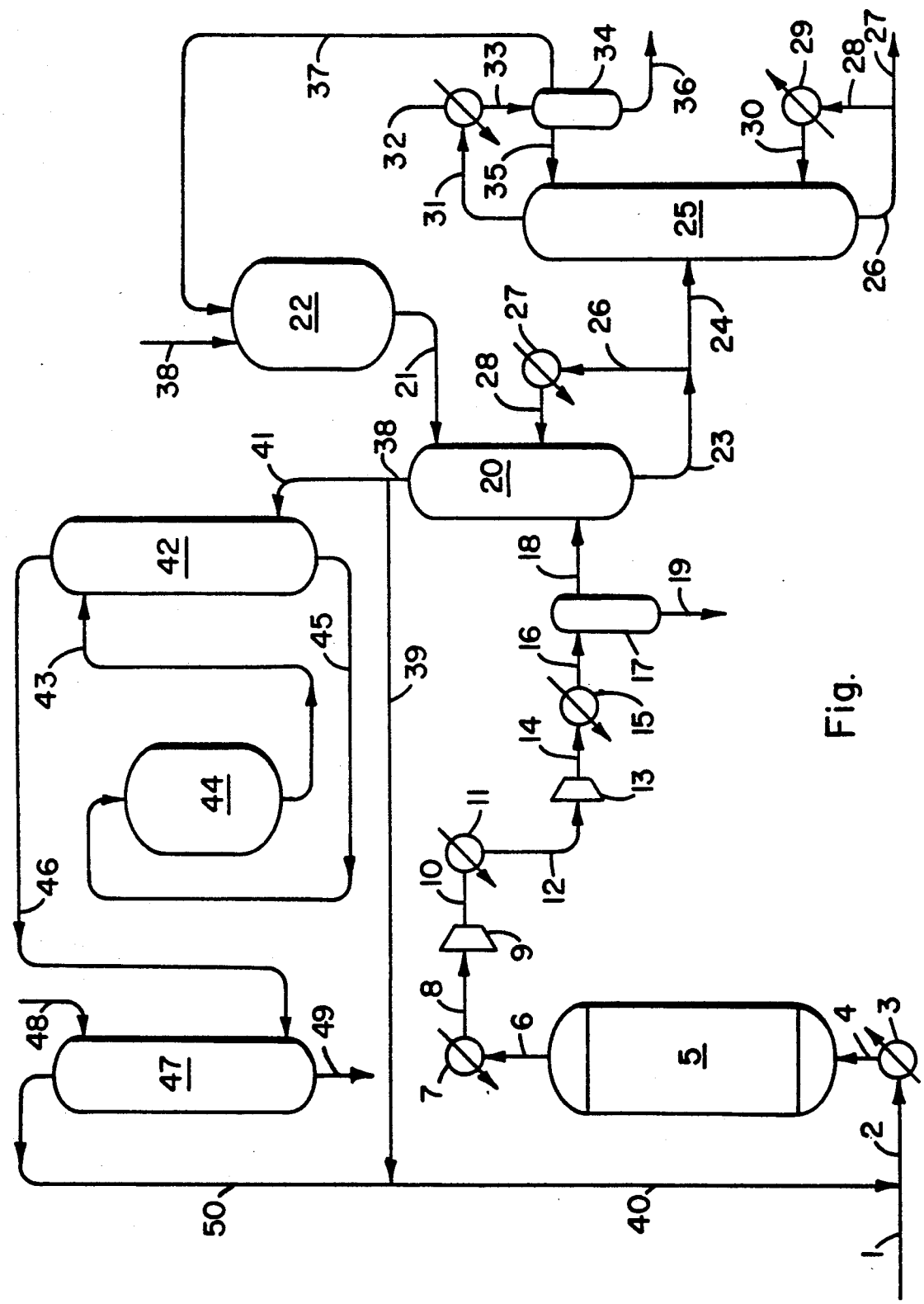

RECOVERY OF 3,4-EPOXY-1-BUTENE FROM 1,3-BUTADIENE OXIDATION EFFLUENTS

This invention pertains to the recovery of 3,4-epoxy-1-butene from an oxidation effluent comprising 3,4-epoxy-1-butene, 1,3-butadiene, an inert gas and oxygen produced by the selective oxidation of 1,3-butadiene. More specifically, one embodiment of the present invention pertains to a process wherein the aforesaid oxidation effluent is intimately contacted with liquid 1,3-butadiene in an absorption zone to obtain a solution of 3,4-epoxy-1-butene in 1,3-butadiene. Another embodiment of the invention pertains to the utilization of the 3,4-epoxy-1-butene recovery process as a means for accurately regulating the amount of 1,3-butadiene in the gas fed to an oxidation zone wherein 1,3-butadiene is selectively oxidized to 3,4-epoxy-1-butene.

U.S. Pat. Nos. 4,897,498 and 4,950,773 disclose processes for the manufacture of 3,4-epoxy-1-butene (referred to herein as EpB) by the selective epoxidation of 1,3-butadiene (referred to herein as butadiene) wherein butadiene is contacted with an oxygen containing gas in the presence of certain silver catalysts. To achieve high yields of EpB (based on the butadiene consumed), especially when operating on a commercial scale, it is necessary to maintain the conversion of the butadiene at relatively low levels, e.g., from about 2 to 20 mole percent based on the butadiene fed to the epoxidation zone. The epoxidation effluent thus contains significant amounts of butadiene which must be recovered and recycled to the epoxidation zone. Obtaining a high yield of EpB also requires the presence of an inert gas diluent in the gas feed to the epoxidation zone. For example, an inert gas such as methane, nitrogen, helium or the like typically constitutes from about 50 to 80 mole percent of the gas feed to the epoxidation zone.

EpB is a very reactive compound which can be used to manufacture a variety of chemicals. Due to its reactivity, the recovery of EpB from epoxidation effluents must be performed under mild conditions to avoid the conversion of EpB to other undesired compounds such as butenediols and oligomers. It is possible to recover EpB directly from the epoxidation effluent by compressing the gaseous effluent to pressures sufficiently high to liquify the EpB. However, the compression of the effluent would require the use of a series of compressors and heat exchangers to remove the heat of compression and maintain the EpB at a temperature which would minimize by product formation.

The recovery of gaseous products by absorption techniques wherein a gaseous stream is contacted with a liquid absorbent, also referred to as an extractant or solvent, is well known. For example, in ethylene oxide processes wherein ethylene is epoxidized to ethylene oxide, water is used to absorb the ethylene oxide contained in the gaseous epoxidation effluent. A significant amount of the ethylene oxide reacts with the water to produce ethylene glycol. Since the objective of EpB manufacturing processes is the recovery of as much EpB as possible and since EpB has very limited water solubility, water is not a practical absorbent for the recovery of EpB.

An absorbent/solvent suitable for use in the recovery of EpB must be inert with respect to both EpB and to oxidation in the epoxidation zone. Saturated hydrocarbons such as pentane, hexane, cyclohexane, heptane, and the like form azeotropes with EpB which makes separation of EpB from the solvent quite difficult. The use of aromatic hydrocarbons, such as benzene, toluene, or xylene, and their presence in the EpB production system causes a decrease in the activity of the silver epoxidation catalyst due to complexation with the silver. Additionally, the temperatures that must be employed with these solvents to recover all the butadiene in the pressure distillation column cause losses of EpB due to polymerization and reaction with active hydrogen compounds, e.g., water, butenediols, and/or higher EpB adducts.

We have found that EpB, as well as butadiene, can be recovered from a substantially gaseous, epoxidation effluent comprising EpB, butadiene, oxygen and an inert gas by intimately contacting the effluent with liquid butadiene in an absorption zone. We also have found that by the use of certain conditions within the absorption zone, a vapor effluent containing a predetermined concentration of butadiene may be removed from the absorption zone and utilized as the butadiene feed to the epoxidation zone. One embodiment of our invention therefore pertains to a process for the recovery of EpB from a substantially gaseous effluent from an epoxidation zone wherein butadiene is contacted with an oxygen containing gas in the presence of a catalyst and an inert gas, to produce an epoxidation effluent comprising EpB, butadiene, oxygen and an inert gas which comprises feeding the effluent to an absorption vessel wherein the effluent is intimately contacted with liquid butadiene at a pressure of about 5 to 15 bars and a temperature of about 0° to 30° C. to obtain:

(1) a vapor effluent comprising butadiene and the oxygen and inert gas from the upper section of the absorption vessel; and (2) a liquid effluent comprising EpB and butadiene from the lower section of the absorption vessel.

The use of butadiene as the adsorbent is economically advantageous as compared to the use of other organic materials which are extraneous to the EpB production system. For example, the use of another absorbent would increase costs due to the additional equipment required for its recovery in addition to the added cost of the absorbent material itself.

The accompanying Figure is a process flow diagram illustrating an EpB production system embodying the principles of the processes of the present invention. While the present invention is susceptible to embodiment in various forms, there is shown in the Figure and hereinafter described in detail preferred embodiments of the invention. However, the present disclosure is to be considered as an exemplification of the invention without limitation to the specific embodiments illustrated. The pressures referred to herein are given in bars absolute.

The present invention may be used in combination with any epoxidation process wherein butadiene is contacted with an oxygen containing gas in the presence of a catalyst and an inert gas to produce an epoxidation effluent comprising EpB, butadiene, oxygen and an inert gas. The silver catalyzed, epoxidation processes described in U.S. Pat. Nos. 4,897,498 and 4,950,773 are typical of those which may be employed in the epoxidation zone. The epoxidation zone comprises one or more reactors of any design that allows removal of the heat of reaction in order to prevent an exothermic temperature excursion from occurring. For example, a shell and tube design, typically used for ethylene oxide production, may be employed. Other types of reactor designs include multi staged adiabatic reactors, fluidized bed reactors, moving or transport bed reactors and the like.

The feed to the epoxidation zone comprises butadiene, an oxygen containing gas and an inert diluent gas in various proportions. Generally, any oxygen ($O_2$) concentration up to the explosive limit can be used. For example, when using nitrogen as the inert gas, the maximum oxygen concentration normally is in the range of about 9 mole percent. Higher oxygen concentrations, e.g., up to about 18 mole percent may be employed using methane as the inert diluent. The butadiene concentration typically is about 8 to 30 mole percent. The butadiene:oxygen mole ratio in the feed normally is maintained within the range of about 0.5:1 to 5:1. The inert diluent gas usually constitutes about 50 to 80 mole percent of the total feed to the epoxidation zone. Normally, the feed also include a small amount, e.g., 1 to 40 parts per million (ppm) of a halide source such as 1,2-dichloroethane. Various other organic halides which may be used are described in U.S. Pat. No. 4,950,773. The concentration of the organic halide in the feed more commonly is in the range of 2 to 10 ppm. The feed also may contain minor amounts, e.g., less than a total of 5 mole percent, of impurities such as water and carbon dioxide.

Although the reactor of the epoxidation zone may be operated at pressures ranging from 0.1 to 20 bars, pressures in the range of about 1 to 3 bars normally are used. The epoxidation feed typically is heated to about 195° to 240° C. in a pre heater prior to entering the epoxidation reactor. The temperature of the epoxidation effluent is maintained at about 210° to 260° C., preferably about 230° to 240° C., by adjusting the pre heater temperature and/or the concentration of oxygen and/or the organic halide in the feed.

The silver catalysts described in U. S. Pat. No. 4,897,498 are examples of the epoxidation catalysts which may be used to convert butadiene to EpB. The catalyst preferably is a supported, cesium promoted, silver catalyst.

The gaseous epoxidation effluent typically comprises about 0.5 to 6 mole percent EpB, about 7 to 26 mole percent butadiene, about 4 to 16 mole percent oxygen and about 50 to 80 mole percent inert gas. The effluent also contains a total of about 0.5 to 5 mole percent of water, carbon dioxide, acrolein, furan, vinylacetaldehyde, and crotonaldehyde, formed in the epoxidation zone. Unconsumed organic halide also is present in the epoxidation effluent. Typically the overall selectivity to EpB is 90-95%. As used herein, the percent conversion of butadiene is:

$$\frac{\text{Moles butadiene converted}}{\text{Moles butadiene fed}} \times 100$$

and the percent selectivity to 3,4-epoxy-1-butene is:

$$\frac{\text{Moles butadiene converted to 3,4-epoxy-1-butene}}{\text{Moles butadiene converted}} \times 100$$

The epoxidation effluent is fed to a cooling/compression zone comprising one or more heat exchangers and one or more compressors wherein the effluent is pressurized to a pressure of about 5 to 15 bars absolute and cooled to a temperature of about 0° to 60° C. The cooling/compression zone may include a gas/liquid separator to remove any condensed liquids, e.g., water and/or butenediols (3-butene-1,2-diol and 2-butene-1,4-diol), from the pressurized and cooled effluent prior to feeding it to the absorption zone.

The absorption zone comprises a columnar, pressure vessel containing trays or a packing material which facilitates intimate gas/liquid contact. Examples of suitable packing material include Koch-Sulzer packing, Pall rings, Berl saddles, and Penn State packing. The absorption vessel normally is provided with means, such as a disengaging space above the packing, to prevent or minimize entrainment of liquids in the gas stream removed from the upper section thereof. The pressurized, cooled, substantially gaseous, epoxidation effluent is fed to the lower section of the absorption vessel, preferably near the bottom of the vessel. Liquid butadiene is fed to the upper section, preferably near the top, of the absorption vessel and flows downward, thereby absorbing or scrubbing the EpB component from the upwardly-flowing epoxidation effluent. A solution of EpB in butadiene is removed from the base of the absorption vessel and a vapor comprising butadiene and the inert gas, oxygen and carbon dioxide components of the epoxidation effluent is removed from the top of the vessel.

As stated hereinabove, the epoxidation effluent is intimately contacted with liquid butadiene in the absorption zone at a pressure of about 5 to 15 bars and a temperature of about 0° to 30° C. The absorption zone preferably is operated at pressures and temperatures of about 6 to 13 bars and about 2 to 22° C. to minimize the reaction of the EpB with the minor amounts of active hydrogen compounds present. In a preferred embodiment of our invention, the particular combination of pressure and temperature are selected to provide a predetermined concentration, e.g., about 8 to 30, preferably about 10 to 25, mole percent, of butadiene in the vapor effluent removed from the absorption vessel. The butadiene-containing vapor effluent thus obtained can be recycled, directly or indirectly, to the epoxidation zone and provide all of the butadiene reactant for the epoxidation reaction.

The amount of liquid butadiene fed to the absorption vessel can vary substantially depending, for example, on the particular vessel, packing material and conditions employed and the feed rate and composition of the epoxidation effluent fed. Generally, the weight ratio of the butadiene feed to epoxidation effluent feed is in the range of about 0.05:1 to about 0.5:1. The temperature of the liquid butadiene fed typically is in the range of about 0° to 30° C.

A liquid effluent (absorption underflow) comprising a solution of EpB in butadiene is removed from the base of the absorption vessel and is fed to a butadiene recovery zone. A portion, e.g., up to about 95 volume percent, of the underflow may be recycled to the absorption vessel. The recycle stream optionally may be cooled by means of a heat exchanger and returned to the lower section of the absorption vessel to control or regulate the temperature therein. The concentration of EpB in the absorption underflow stream may vary substantially, e.g., from about 5 to 75 weight percent based on the total weight of the stream. Normally, the EpB concentration is in the range of about 40 to 70 weight percent (same basis).

The butadiene recovery zone comprises a distillation vessel, e.g., a column, a heat source at the base of the vessel, cooling means to condense vapor removed from the top of the vessel and a separator to separate water from the condensed liquid. The absorption column underflow may be fed to the mid-section of the butadiene recovery column to obtain (1) a gas effluent comprising butadiene from the upper section of the column and (2) a liquid effluent comprising crude EpB from the lower section of the column. The gas effluent contains a minor amount of water which may be removed from the EpB production system by condensing the effluent to obtain a two-phase, liquid mixture and separating the aqueous phase from the butadiene phase. Water and butadiene form a constant boiling mixture (azeotrope) having a boiling point of approximately 57° C. at 4.46 bars pressure. The water removal may be enhanced by recycling a portion, e.g., up to 80 weight percent, of the condensed butadiene phase to the upper section of the butadiene recovery vessel. The water-depleted butadiene stream removed from the butadiene recovery zone may be recycled, directly or indirectly, to the absorption zone along with fresh butadiene.

A second embodiment of our invention therefore concerns a process for the recovery of EpB from a substantially-gaseous, epoxidation effluent from an epoxidation zone wherein butadiene is contacted with an oxygen-containing gas in the presence of a catalyst and an inert gas to produce an epoxidation effluent comprising EpB, butadiene and an inert gas which comprises the steps of:

(A) feeding the effluent to an absorption vessel wherein the effluent is intimately contacted with liquid butadiene at a pressure of about 5 to 15 bars and a temperature of about 0° to 30° C. to obtain:
(1) a vapor effluent comprising butadiene and the inert gas and oxygen from the upper section of the absorption vessel; and
(2) a liquid effluent comprising EpB and butadiene from the lower section of the absorption vessel;
(B) feeding the effluent of step (A)(2) to a butadiene recovery vessel operated at a pressure of about 2 to 6 bars and a temperature over the range of about 5 to 150 to obtain:
(1) a gas effluent comprising butadiene from t he upper section of the column; and
(2) a liquid effluent comprising crude EpB from the lower section of the column;
(C) condensing the gas effluent of step (B)(1) to obtain a two-phase mixture comprising water and butadiene and separating water from the two-phase mixture to obtain a water-depleted butadiene stream; and
(D) recovering the water depleted butadiene.

The conditions employed within the butadiene recovery column may vary significantly depending on the particular apparatus employed. The pressures and temperatures normally are within the range of about 2.5 to 4 bars and 5° to 120° C. The column preferably is operated at a column base pressure and temperature of about 2.5 to 4 bars and 100° to 120° C. and a column head pressure and temperature of about 2.5 to 4 bars and 5° to 40° C. To prevent the formation of butadiene polymerization products, the butadiene recovery preferably is carried out in the presence of a polymerization inhibitor, such as a phenolic compound, e.g., tertiary butyl catechol or a non-phenolic compound, e.g., Actrene 230 inhibitor supplied by Exxon. The polymerization inhibitor may be added to the upper section of the butadiene recovery column. For example, we have found that the formation of low molecular weight, butadiene polymerization products is substantially suppressed by the addition of about 300 to 400 ppm Actrene 230 inhibitor, based on the amount of vapor removed from the column, to the top of the butadiene recovery column by means of a low flow addition device such as a syringe pump. The inhibitor also may be added to the absorption vessel, e.g., with the liquid butadiene feed, and transported to the butadiene recovery zone in the liquid effluent stream obtained from the absorption vessel to reduce polymer formation in the transfer lines and tanks.

The liquid underflow obtained from the butadiene recovery zone comprises EpB, typically 90 to 99 weight percent EpB, and minor amounts of butadiene, vinyl acetaldehyde, butenediols, vinylcyclohexene, crotonaldehyde and higher boiling impurities. This crude EpB may be further purified by distillation wherein EpB is taken overhead and most of the impurities are removed from the base of the distillation column.

As described hereinabove, the absorption zone may be operated to provide a vapor effluent containing a predetermined amount of butadiene which can be fed to, and provide all of the butadiene reactant for, the epoxidation zone. This advantageous method of supplying the butadiene reactant to the epoxidation zone constitutes another embodiment of the present invention. This embodiment concerns a process for the manufacture and separation of EpB which comprises the steps of:

I. feeding a gas comprising about 8 to 30 mole percent butadiene, about 5 to 18 mole percent oxygen and about 50 to 80 mole percent of an inert material to an epoxidation zone wherein butadiene is epoxidized to EpB;

II. removing from the epoxidation zone a gaseous epoxidation effluent comprising about 0.5 to 6 mole percent EpB, about 7 to 26 weight percent butadiene, about 4 to 16 mole percent oxygen and about 50 to 80 weight percent inert gas;

III. feeding the gaseous epoxidation effluent to a cooling/compression zone wherein the effluent is pressurized to a pressure of about 5 to 15 bars and cooled to a temperature of about 0° to 60° C.;

IV. feeding the effluent obtained from step (III) to an absorption vessel wherein the effluent is intimately contacted with liquid butadiene at a pressure of about 5 to 15 bars and a temperature of about 0° to 30° C. to obtain:
(1) a vapor effluent comprising the inert gas and about 8 to 30 mole percent butadiene from the upper section of the absorption vessel; and
(2) a liquid effluent comprising EpB and butadiene from the lower section of the absorption vessel;

V. feeding the effluent of step IV.(1) to the epoxidation zone;

wherein the butadiene fed in step I. is provided by the effluent of step IV.(1). The 5-step embodiment may include an additional step wherein the effluent of step IV.(1) is fed to a carbon dioxide removal zone as described hereinafter.

We have found that the presence of significant amounts of carbon dioxide in the gas fed to the epoxidation zone detrimentally affects the activity of silver epoxidation catalysts, i.e., causes a decrease in the epoxidation rate. For example, when the feed gas contains 2 mole percent carbon dioxide, the EpB production rate is about 55% of that achieved when the feed contains essentially no carbon dioxide, i.e., less than about 1000 ppm carbon dioxide. When the feed gas contains only 1 mole percent carbon dioxide, the EpB production rate is about 75% of the rate achieved when the feed contains essentially no carbon dioxide. Therefore, the butadiene-containing effluent gas optionally is passed through a carbon dioxide removal zone wherein the carbon dioxide concentration of the gas is reduced to less than about 0.5 mole percent, preferably less than about 0.2 mole percent and most preferably to less than about 1000 ppm. Carbon dioxide removal may be accomplished by various known means such as by absorption using alkali and alkaline earth hydroxides and carbonates such as sodium and potassium hydroxides and carbonates, amines such as monoethanolamine and diethanolamine and size exclusion techniques using membranes or molecular sieves.

The carbon dioxide removal zone may comprise, for example, an absorption vessel wherein the gas is intimately contacted with an aqueous solution of an alkali metal hydroxide such as potassium hydroxide and from which a carbon dioxide-depleted gas effluent is removed. Thus, the effluent gas is fed to the bottom section and the aqueous solution of the alkali metal hydroxide, e.g., a 30 to 50 weight percent aqueous solution of potassium hydroxide, is fed to the upper section of the carbon dioxide absorption vessel containing an appropriate packing material or trays. The pressure within the vessel typically is about 5 to 8 bars. If necessary, the carbon dioxide removal zone may include an alkali removal vessel (scrubber) wherein the carbon dioxide-depleted gas stream is contacted (scrubbed) with water to remove any alkali metal hydroxide or carbonate entrained in the gas removed from the carbon dioxide absorption vessel. Typical pressures and temperatures within the scrubber vessel are about 2 to 8 bars and 5° to 110° C.

Since oxygen is consumed in the epoxidation zone, the oxygen content of the butadiene containing effluent gas obtained from the EpB absorption zone (or the carbon dioxide removal zone) is supplemented by an oxygen feed prior to feeding the gas to the epoxidation zone. Normally, an organic halide (discussed hereinabove) also is added to the effluent gas.

Referring to the accompanying Figure, a mixture comprising butadiene, oxygen, an inert gas and an organic halide is fed by conduit 2 to heat exchanger 3 wherein the mixture is preheated to a temperature of about 195° to 240° C. and then is fed via conduit 4 to epoxidation reactor 5. The epoxidation reactor may contain a plurality of steel tube packed with a silver catalyst such as a cesium-promoted, supported, silver catalyst. The gas feed passes through the catalyst-containing steel tubes wherein butadiene is selectively oxidized to EpB and exits the epoxidation reactor through conduit 6. A heat exchange fluid is passed over the exterior of the reactor tubes to remove the heat of reaction. The temperature and pressure within conduit 6 typically is about 1 to 4 bars and 210° to 260° C.

The epoxidation effluent is fed to heat exchangers 7, 11, and 15 and compressors 9 and 13 by conduits 6, 8, 10, 12 and 14 wherein the temperature of the effluent stream is reduced to about 0° to 60° C. and the pressure is increased to about 5 to 15 bars. The cooled and pressurized effluent is transported by conduit 16 to gas/liquid separator 17 and then through conduit 18 to absorber 20. The function of gas/liquid separator 17 is the removal of materials such as butenediols and water which are liquified by the cooling and compression of the epoxidation effluent stream.

Liquid butadiene is fed from butadiene recovery tank 22 through conduit 21 to the upper section of absorber 20 which contains a suitable packing material to provide intimate contact between the effluent fed by line 18 and liquid butadiene fed by line 21. The pressure and temperature within absorber 20 are within the ranges of about 5 to 15 bars and 0° to 30° C., provided that the combination of pressure and temperature maintains a liquid phase within the absorber. The conditions of pressure and temperature also are controlled to provide a predetermined concentration of butadiene in the gaseous effluent removed from the top of the absorber.

A liquid effluent comprising a solution of EpB in butadiene is removed from the base of absorber 20 and transported via conduits 23 and 24 to the mid-section of butadiene recovery column 25. A portion, e.g., up to about 95 weight percent, of the liquid effluent stream may be recycled through conduits 26, heat exchanger 27 and conduit 28 to absorber 20. This recycle stream functions to provide additional cooling of the contents of the absorber.

The concentration of EpB in the liquid solution fed by line 24 to column 25 typically is about 20 to 40 weight percent based on the total weight of the solution. Column 25 typically is equipped with tray or a packing material and is operated at a base pressure and temperature of about 2.5 to 4 bars and 100° to 120° C. and a head (top) temperature of about 2.5 to 4 bars and 5° to 40° C. to vaporize substantially all of the butadiene fed. A liquid stream of crude EpB is removed from column 25 and from the EpB production system via conduits 26 and 27. This stream may be further refined by one or more distillations to increase the purity of the EpB, e.g., up to 99+%.

The heat required to vaporize butadiene in column 25 is provided by recycling a portion, e.g., up to 95 weight percent, of the liquid stream to column 25 by means of conduit 28, heat exchanger (reboiler) 29 and conduit 30. A vapor comprised of butadiene and a minor amount of water is removed from column 25 through conduit 31, condensed in heat exchanger 32 and fed by conduit 33 to water separator 34. Water collects in the lower section of separator 34 and is removed from the production system by conduit 36. Separation of butadiene and water from the other materials fed to column 25 is enhanced by recycling a portion, e.g., from about 50 to 95 weight percent, of the condensed butadiene to the column via line 35. The remainder of the condensed butadiene is transported by conduit 37 to butadiene recovery tank 22. Fresh butadiene also is fed to tank 22 by line 38. A butadiene polymerization inhibitor also may be added to tank 22.

A vapor effluent comprising butadiene, an inert gas, i.e., the inert gas fed to epoxidation reactor 5, and oxygen is removed from absorber 20 via conduit 38. Normally, the butadiene content of the vapor effluent is within the range of about 8 to 30, preferably about 10 to 25, mole percent. The butadiene containing vapor effluent is conveyed to epoxidation reactor 5 by conduits 39, 40, 2 and 4 and preheater 3 and provides the butadiene reactant for the epoxidation reaction. When using this mode of direct recycle to the epoxidation reactor, a portion of the stream of conduit 39 is purged from the production system to prevent an excessive accumulation of carbon dioxide in the system. Oxygen is combined via conduit 1 with the effluent of line 40 to bring the concentration of oxygen in the reactor feed to about 5 to 18 mole percent.

Alternatively, the vapor effluent removed from EpB absorber 20 via line 38 is transported to a carbon dioxide removal zone comprising carbon dioxide absorber 42, aqueous caustic tank 44 and scrubber 47. The vapor effluent is fed by conduit 41 to the lower section of absorber 42 which contains an appropriate packing material. An aqueous solution of an alkali metal hydroxide (caustic) is fed via conduit 43 to the upper section of absorber 42 from aqueous caustic tank 44. Carbon dioxide is absorbed by the conversion of the alkali metal hydroxide to a carbonate. The aqueous solution of alkali metal hydroxide/carbonate is removed from absorber 42 and returned to tank 44 by line 45. A carbon dioxide-depleted vapor is removed from the top of absorber 42 and conveyed by conduit 46 to the lower section of scrubber 47 wherein any alkali metal compound entrained in the carbon dioxide depleted vapor is removed. Water is fed by means of conduit 48 to the upper section of scrubber 47 and removed from the bottom of the scrubber through line 49. An alkali-free vapor stream is removed from the top of the scrubber and transported via lines 50, 40, 2 and 4 and preheater 3 to the epoxidation reactor as described previously.

The processes provided by the present invention are further illustrated by the following example using the EpB production system described in the Figure. The flow rates are given in parts by weight. The epoxidation reactor employed fixed beds of the cesium-promoted, supported silver catalyst described in U.S. Pat. No. 4,897,498.

A gas mixture comprising methane (inert gas), oxygen, butadiene, water and 4–5 ppm 1,2 -dichloroethane is heated to 215° C. in preheater 3 and fed by line 4 to epoxidation reactor 5 at a rate of 2433 parts per hour at a pressure of 1.5 bars. The epoxidation effluent gas comprising methane, oxygen, butadiene, water, carbon dioxide, EpB and high boilers are removed from reactor 5 via line 6 at the rate of 2433 parts per hour and transported through heat exchangers 7, 11 and 15 and compressors 9 and 13 by lines 6, 8, 10, 12, 14 and 16 to gas/liquid separator 17. Water and butenediols are removed from separator 17 at rates of 9 and 2 parts per hour, respectively.

The epoxidation effluent gas (depleted in butenediols) is fed via conduit 18 to the side and near the bottom of EpB absorber 20 which consists of a 1.8 m section of stainless steel pipe having an inside diameter of approximately 10 cm. The absorber is packed with 14.1 liters of 6.35 mm Penn State packing except for a 0.5 m vacant space at the top. Liquid butadiene is fed at a pressure of 11.4 bars and a temperature of 25° C. by conduit 21 to the side and near the top of absorber 20 at a rate of 466 parts per hour. The pressure and temperature within the absorber are 11.4 bars and 12° C. A liquid comprising butadiene, EpB, water, butenediols and high boilers is removed from absorber 20 by conduit 23 and fed through conduit 24 to the mid-section of butadiene recovery column 25 at a rate of 461 parts per hour. A portion of the conduit 23 stream is removed by line 26, cooled in heat exchanger 27 and recycled via conduit 28 to the lower section of absorber 20 at a rate of 4149 parts per hour.

Column 25 is operated at a base pressure and temperature of 3.9 bar and 120° C. and a top pressure and temperature of 3.9 bar and 38° C. A liquid stream comprising EpB, butenediols, and high boilers is removed from the base of column 25 and from the production system via conduits 26 and 27 at a rate of 88 parts per hour. A portion of the liquid stream of line 26 is removed by line 28, passed through heat exchanger 29 and fed to the lower section of column 25 to maintain the base temperature of 120° C. therein. The crude EpB product of line 27 may be distilled to obtain an overhead EpB product having a purity in excess of 99%.

A vapor effluent comprising methane, oxygen, carbon dioxide and butadiene is removed from absorber 20 through line 38 at a rate of 2427 parts per hour and is fed by line 41 to the lower sidewall of carbon dioxide absorber 42. The vapor effluent may be returned directly to epoxidation reactor 5 via lines 38, 39, 40, 2 and 4 and preheater 3 although the carbon dioxide present in the vapor has been found to adversely affect the epoxidation reaction. The carbon dioxide absorber consists of a 1.8 m section of stainless steel pipe having an internal diameter of 7.6 cm. An aqueous solution containing approximately 20 weight percent potassium hydroxide/carbonate is fed via conduit 43 to the upper section of, and removed via conduit 45 from the bottom of, absorber 42 at a rate of 249 parts per hour. A carbon dioxide depleted vapor effluent is removed from absorber 42 and fed at a rate of 2426 parts per hour by conduit 46 to the lower section of scrubber 47 wherein any entrained potassium hydroxide/carbonate is removed by water fed through line 48 and removed by line 49.

The vapor effluent from scrubber 47 is transported to reactor 5 by lines 50, 40, 2 and 4 and preheater 4 at a rate of 2368 parts per hour. A portion of the line 40 stream is purged (not shown) from the production system at a rate of 54 parts per hour. A mixture of methane and oxygen is combined with the line 40 stream at a rate of 65 parts per hour.

In the above example, EpB is produced at a rate of 0.57 Kg per liter catalyst per hour at an average butadiene conversion of 8.1% and an overall EpB yield of 89.7%. This EpB production rate is achieved by operating the described EpB production system continuously for a period of time exceeding 300 hours.

The compositions of some of the streams of the preceding example are set forth in Table I wherein the values given are weight percentages based on the total weight of the stream composition, Diols refers to a mixture of 3-butene-1,2-diol and 2-butene-1,4-diol. High Boilers include vinyl acetaldehyde, vinylcyclohexene, crotonaldehyde and high molecular weight compounds.

TABLE I

| Conduit Stream | $CH_4$ | $O_2$ | $CO_2$ | $C_4H_6$ | EpB | $H_2O$ | Diols | High Boilers |
|---|---|---|---|---|---|---|---|---|
| 1 | 43.1 | 56.9 | 0 | 0 | 0 | 0 | 0 | 0 |
| 4 | 51.1 | 10.9 | 0 | 37.7 | 0 | 0.3 | 0 | 0 |
| 16 | 51.1 | 9.5 | 0.5 | 34.7 | 3.5 | 0.5 | 0.1 | <0.1 |
| 24 | 0 | 0 | 0 | 80.5 | 18.7 | 0.4 | 0.2 | 0.2 |
| 27 | 0 | 0 | 0 | 0 | 97.7 | 0 | 1.1 | 1.1 |
| 38 | 51.3 | 9.6 | 0.5 | 38.6 | 0 | 0 | 0 | 0 |
| 50 | 51.3 | 9.6 | 0 | 38.8 | 0 | 0.3 | 0 | 0 |

As has been described hereinabove, one embodiment of our invention is the use of the EpB absorber as the source of the butadiene reactant fed to the epoxidation reactor. For this purpose, the mole percent butadiene in the vapor effluent from the EpB absorber normally is maintained between about 8 and 30, preferably between about 10 and 25, mole percent. A wide variety of combinations of pressure and temperature may be employed within the absorber to produce vapor effluents containing such concentrations of butadiene. Table II shows the pressures (in bars absolute) which are required when using temperatures of −20° C. to 30° C. to produce vapor effluents containing 15, 20 and 25 mole percent butadiene.

TABLE II

| Temperature | Pressure Required To Maintain Butadiene Concentrations of: | | |
|---|---|---|---|
| | 15.0% | 20.0% | 25.0% |
| −20 | 3.53 | 2.65 | 2.12 |
| −15 | 4.40 | 3.30 | 2.64 |
| −10 | 5.42 | 4.06 | 3.25 |
| −5 | 6.62 | 4.96 | 3.97 |
| 0 | 8.01 | 6.01 | 4.81 |
| 5 | 9.63 | 7.22 | 5.78 |
| 10 | 11.48 | 8.61 | 6.89 |
| 15 | 13.60 | 10.20 | 8.16 |
| 20 | 16.00 | 12.00 | 9.60 |
| 25 | 18.72 | 14.04 | 11.23 |
| 30 | 21.77 | 16.33 | 13.06 |

The EpB absorber preferably is operated within the range of 0° to 30° C. and 6 to 13 bars since cooling the epoxidation effluent to less than 0° C. is costly due to the equipment required and the increased operating costs involved and pressurizing the effluent significantly above 13 bars can cause a decrease in the overall yield of EpB due to its conversion to other compounds in the cooling/compression zone.

The invention has been described in detail with particular reference to preferred embodiments thereof, but it will be understood that variations and modifications may be effected within the spirit and scope of the invention.

We claim:

1. Process for the recovery of EpB from a substantially-gaseous, effluent from an epoxidation zone wherein butadiene is contacted with an oxygen-containing gas in the presence of a catalyst and an inert gas to produce an epoxidation effluent comprising EpB, butadiene, oxygen and an inert gas which comprises feeding the effluent to an absorption vessel wherein the effluent is intimately contacted with liquid butadiene at a pressure of about 5 to 15 bars and a temperature of about 0° to 30° C. to obtain:
   (1) a vapor effluent comprising butadiene and the oxygen and inert gas from the upper section of the absorption vessel; and
   (2) a liquid effluent comprising EpB and butadiene from the lower section of the absorption vessel;
wherein EpB is 3,4-epoxy-1-butene and butadiene is 1,3-butadiene.

2. Process according to claim 1 wherein the epoxidation effluent comprises about 0.5 to 6 mole percent EpB, about 7 to 26 mole percent butadiene, about 4 to 16 mole percent oxygen and about 50 to 80 mole percent inert gas and the amount of liquid butadiene employed is about 0.05 to 0.5 parts by weight per part by weight epoxidation effluent.

3. Process for the recovery of EpB from a substantially-gaseous, effluent from an epoxidation zone wherein butadiene is contacted with an oxygen-containing gas in the presence of a silver catalyst and an inert gas to produce an epoxidation effluent comprising about 0.5 to 6 mole percent EpB, about 7 to 26 mole percent butadiene, about 4 to 16 mole percent oxygen and about 50 to 80 mole percent inert gas which comprises feeding the effluent to an absorption vessel wherein the effluent is intimately contacted with liquid butadiene at a pressure of about 6 to 13 bars and a temperature of about 2° to 22° C. to obtain:
   (1) a vapor effluent comprising butadiene and the oxygen and inert gas from the upper section of the absorption vessel; and
   (2) a liquid effluent comprising EpB and butadiene from the lower section of the absorption vessel;
wherein EpB is 3,4-epoxy-1-butene and butadiene is 1,3-butadiene.

4. Process according to claim 3 wherein vapor effluent (1) contains about 10 to 25 mole percent butadiene and liquid effluent (2) contains about 20 to 40 weight percent EpB.

5. Process for the recovery of EpB from a substantially-gaseous, epoxidation effluent from an epoxidation zone wherein butadiene is contacted with an oxygen-containing gas in the presence of a catalyst and an inert gas to produce an epoxidation effluent comprising EpB, butadiene, oxygen and an inert gas which comprises the steps of:
   (A) feeding the effluent to an absorption vessel wherein the effluent is intimately contacted with liquid butadiene at a pressure of about 5 to 15 bars and a temperature of about 0° to 30° C. to obtain:
      (1) a vapor effluent comprising the inert gas, oxygen and butadiene from the upper section of the absorption vessel; and
      (2) a liquid effluent comprising EpB, water and butadiene from the lower section of the absorption vessel;
   (B) feeding the effluent of step (A)(2) to a butadiene recovery vessel operated at a pressure of about 2 to 6 bars and a temperature of about 5° to 150° C. to obtain:
      (1) a vapor effluent comprising butadiene and water from the upper section of the column; and
      (2) a liquid effluent comprising crude EpB from the lower section of the column;
   (C) condensing the vapor effluent of step (B)(1) to obtain a two-phase mixture comprising water and butadiene and separating water from the two-phase mixture to obtain a water depleted butadiene stream; and
   (D) recovering the water depleted butadiene;
wherein EpB is 3,4-epoxy-1-butene and butadiene is 1,3-butadiene.

6. Process according to claim 5 wherein the epoxidation effluent comprises about 0.5 to 6 mole percent EpB, about 9 to 26 mole percent butadiene, about 4 to 16 mole percent oxygen and about 50 to 80 mole percent inert gas, the amount of liquid butadiene employed is about 0.05 to 0.5 parts by weight per part by weight epoxidation effluent and liquid effluent (A)(2) contains about 5 to 75 weight percent EpB.

7. Process for the recovery of EpB from a substantially-gaseous, epoxidation effluent from an epoxidation zone wherein butadiene is contacted with an oxygen-containing gas in the presence of a silver catalyst and an inert gas to produce an epoxidation effluent comprising about 0.5 to 6 mole percent EpB, about 7 to 26 mole percent butadiene, about 4 to 16 mole percent oxygen and about 50 to 80 mole percent inert gas which comprises the steps of:
   (A) feeding the effluent to an absorption vessel wherein the effluent is intimately contacted with liquid butadiene at a pressure of about 6 to 13 bars and a temperature of about 2' to 22° C. to obtain:
      (1) a vapor effluent comprising butadiene and the oxygen and inert gas from the upper section of the absorption vessel; and (2) a liquid effluent comprising about 20 to 40 weight percent EpB and butadiene from the lower section of the absorption vessel;

(B) feeding the effluent of step (A)(2) to a butadiene recovery column operated at a column base pressure and temperature of about 2.5 to 4 bars and about 100° to 120° C. and at a column head pressure and temperature of about 2.5 to 4 bars and about 5° to 40° C. to obtain:

(1) a vapor effluent comprising butadiene from the upper section of the column; and (2) a liquid effluent comprising crude EpB from the lower section of the column;

(C) condensing the vapor effluent of step (B)(1) to obtain a two-phase mixture comprising water and butadiene and separating water from the two-phase mixture to obtain a water-depleted butadiene stream; and (D) recovering the water-depleted butadiene;

wherein EpB is 3,4-epoxy-1-butene and butadiene is 1,3-butadiene.

8. Process for the manufacture and separation of EpB which comprises the steps of:

I. feeding a gas comprising about 8 to 30 mole percent butadiene, about 5 to 18 mole percent oxygen and about 50 to 80 mole percent of an inert material to an epoxidation zone wherein butadiene is epoxidized to EpB in the presence of a silver catalyst;

II. removing from the epoxidation zone a gaseous epoxidation effluent comprising about 0.5 to 6 mole percent EpB, about 7 to 26 mole percent butadiene, about 4 to 16 mole percent oxygen and about 50 to 80 mole percent inert gas;

III. feeding the gaseous epoxidation effluent to a cooling/compression zone wherein the effluent is pressurized to a pressure of about 5 to 15 bars and cooled to a temperature of about 0° to 60° C.;

IV. feeding the effluent obtained from step (III) to an absorption vessel wherein the effluent is intimately contacted with liquid butadiene at a pressure of about 5 to 15 bars and a temperature of about 0° to 30° C. to obtain:

(1) a vapor effluent comprising the inert gas and oxygen and about 8 to 30 mole percent butadiene from the upper section of the absorption vessel; and (2) a liquid effluent comprising EpB and butadiene from the lower section of the absorption vessel; and V. feeding the effluent of step IV.(1) to the epoxidation zone;

wherein the butadiene fed in step I. is provided by the effluent of step IV.(1), EpB is 3,4-epoxy-1-butene and butadiene is 1,3-butadiene.

9. Process according to claim 8 wherein the gas of step I. contains less than about 0.2 mole percent carbon dioxide.

10. Process according to claim 8 wherein the vapor effluent of step IV.(1) is fed to a carbon dioxide removal zone to obtain a carbon dioxide-depleted vapor effluent containing less than about 1000 ppm and the carbon dioxide depleted effluent is fed to the epoxidation zone.

11. Process according to claim 10 wherein the carbon dioxide removal zone comprises an absorption vessel wherein the vapor effluent of step IV.(1) is contacted with an aqueous solution of an alkali metal hydroxide.

12. Process for the manufacture and separation of EpB which comprises the steps of:

I. feeding a gas comprising about 10 to 25 mole percent butadiene, about 5 to 18 mole percent oxygen and about 50 to 80 mole percent of an inert material to an epoxidation zone wherein butadiene is epoxidized to EpB in the presence of a silver catalyst;

II. removing from the epoxidation zone a gaseous epoxidation effluent comprising about 0.5 to 6 mole percent EpB, about 7 to 26 mole percent butadiene, about 4 to 16 mole percent oxygen and about 50 to 80 mole percent inert gas;

III. feeding the gaseous epoxidation effluent to a cooling/compression zone wherein the effluent is pressurized to a pressure of about 6 to 13 bars and cooled to a temperature of about 0° to 60° C.;

IV. feeding the effluent obtained from step (III) to an absorption vessel wherein the effluent is intimately contacted with liquid butadiene at a pressure of about 6 to 13 bars and a temperature of about 2° to 22° C. to obtain:

(1) a vapor effluent comprising the inert gas and oxygen and about 10 to 25 mole percent butadiene from the upper section of the absorption vessel; and (2) a liquid effluent comprising a solution containing about 20 to 40 weight percent EpB in butadiene from the lower section of the absorption vessel; and V. feeding the effluent of step IV.(1) to a carbon dioxide removal zone comprising an absorption vessel wherein the vapor effluent of step IV.(1) is contacted with an aqueous solution of an alkali metal hydroxide to obtain a carbon dioxide-depleted vapor effluent containing less than about 1000 ppm and feeding the carbon dioxide-depleted effluent to the epoxidation zone.

wherein the butadiene fed in step I. is provided by the carbon dioxide-depleted effluent of step V., EpB is 3,4-epoxy1-butene and butadiene is 1,3-butadiene.

* * * * *